(12) United States Patent
Pietrzkowski (10) Patent No.: US 9,271,994 B2
(45) Date of Patent: *Mar. 1, 2016

(54) COMPOSITIONS AND METHODS RELATED TO CALCITRIOL

(71) Applicant: VDF Futureceuticals, Inc., Momence, IL (US)

(72) Inventor: Zbigniew Pietrzkowski, Aliso Viejo, CA (US)

(73) Assignee: VDF Futureceuticals, Inc., Momence, IL (US)

( * ) Notice: Subject to any disclaimer, the term of this patent is extended or adjusted under 35 U.S.C. 154(b) by 48 days.

This patent is subject to a terminal disclaimer.

(21) Appl. No.: 14/454,601

(22) Filed: Aug. 7, 2014

(65) Prior Publication Data

US 2014/0349951 A1 Nov. 27, 2014

Related U.S. Application Data

(62) Division of application No. 12/754,311, filed on Apr. 5, 2010, now Pat. No. 8,809,284.

(60) Provisional application No. 61/166,510, filed on Apr. 3, 2009.

(51) Int. Cl.
| | | |
|---|---|---|
| A61K 31/70 | (2006.01) | |
| A61K 31/715 | (2006.01) | |
| A61K 9/20 | (2006.01) | |
| A61K 31/593 | (2006.01) | |
| A61K 31/7028 | (2006.01) | |

(52) U.S. Cl.
CPC ............ *A61K 31/70* (2013.01); *A61K 9/2054* (2013.01); *A61K 31/593* (2013.01); *A61K 31/7028* (2013.01)

(58) Field of Classification Search
CPC .... A61K 31/70; A61K 31/715; A61K 31/593
USPC ................... 514/23, 25, 54, 64, 167
See application file for complete search history.

(56) References Cited

U.S. PATENT DOCUMENTS

| | | | |
|---|---|---|---|
| 5,962,049 A | 10/1999 | Miljkovic | |
| 5,985,842 A | 11/1999 | Miljkovic | |
| 6,080,425 A | 6/2000 | Miljkovic | |
| 6,696,419 B1 | 2/2004 | Miljkovic | |
| 2001/0051184 A1 | 12/2001 | Heng | |
| 2003/0186891 A1 | 10/2003 | Okano et al. | |
| 2005/0032743 A1* | 2/2005 | Miljkovic | ....................... 514/54 |

FOREIGN PATENT DOCUMENTS

WO 2009087652 A2 7/2009

OTHER PUBLICATIONS

Naghii, M.R., et al., "Comparative Effects of Daily and Weekly Boron Supplementation on Plasma Steroid Hormones and Proinflammatory Cytokines," J. Trace Elem Med Biol., Jan. 2011, Issue. 5, vol. 1, pp. 54-58. (abstract only).

Cross, HS, Nittke T, Peterlik M, "Modulation of vitamin D synthesis and catabolism in colorectal mucosa: a new target for cancer prevention", Anticancer Res., Sep. 2009, 29(9):3705-12, Department of Pathophysiology, Medical University of Vienna.

Cross, HS, Kallay, E, "Regulation of the colonic vitamin D system for prevention of tumor progression: an update", Future Oncol., May 2009, 5(4):493-507, Department of Pathophysiology, Medical University of Vienna.

Nelson, CD, Reinhardt, TA, Thacker, TC, Beitz, DC, Lippolis, JD, "Modulation of the bovine innate immune response by production of 1 alpha, 25-dihydroxyvitamin D (3) in bovine monocytes", J. Dairy Sci. Mar 2010, 93 (3):1041-9, Periparturient Diseases of Cattle Research Unit, Animal Disease Center, Agricultural Research Service, USDA, Ames, IA, USA.

Cross, et al., "The Vitamin D endocrine system of the gut—its possible role in colorectal cancer prevention", J Steroid Biochem Mol. Biol. Oct. 2005, 97 (1-2):121-8, Department of Pathophysiology, Medical University of Vienna.

* cited by examiner

*Primary Examiner* — Michael G Hartley
*Assistant Examiner* — Jagadishwar Samala
(74) *Attorney, Agent, or Firm* — Fish & Tsang LLP (57) ABSTRACT

Contemplated compositions and methods are drawn to use of various boron-containing compounds to temporarily and transiently increase endogenous blood calcitriol concentration. The boron-containing compound is preferably a carbohydrate-boron complex having sufficient stability to achieve measurable quantities of the complex in blood upon oral administration of the complex.

18 Claims, 4 Drawing Sheets

Subjects 5, 2, 4 show increase, S1 no change, and S3 strong reduction (the highest initial blood level=36pg)

Figure 1A

Subjects 4, 1, 2 show increase, and subjects 3 and 5 with initial level 36 and 30 show decrease

Figure 1B

Subjects 6, 2, 3 show decrease, and S 4 and 1 (with the lowest initial point) still show increase

Figure 1C

All subjects show significant increase in the range 1.8-3.2 fold

Figure 1D

Acute increase of blood level of 1,25(OH)2D3 in 5 human subjects treated with 552mg of FrxB 5 randomly selected subjects were treated with FrxB for 2 hours. Serum was collected at 0, 30, 60, 90 and 120 minutes after the treatment. Next, collected serum was analyzed to measure amount of active and pre-active D4

Figure 2A

Acute increase of blood level of 1,25(OH)2D3 in 5 human subjects treated with 552mg of FrxB All five subjects treated with FrxB show increased blood level of active D3 during first 2 hours after the treatment. Average increase is 79%!

COMPOSITIONS AND METHODS RELATED TO CALCITRIOL

This application is a divisional of U.S. application Ser. No. 12/754,311, filed Apr. 5, 2010, which claims priority to U.S. provisional application Ser. No. 61/166,510, filed Apr. 3, 2009, both of which are incorporated by reference herein.

FIELD OF THE INVENTION

The field of the invention is compositions and methods related to modulation of calcitriol (1,25-dihydroxyvitamin $D_3$) concentration in blood/serum of a mammal, and especially to short-term modulations of endogenous calcitriol in human serum.

BACKGROUND OF THE INVENTION

The vitamin $D_3$ endocrine system, besides playing pivotal roles in calcium homeostasis and bone mineral metabolism, is recognized to play a pivotal role in a wide range of fundamental biological functions, and especially in cell differentiation, inhibition of cell growth, and immune function. Vitamin $D_3$ (cholecalciferol) is considered a prohormone, which is converted into the more active form 25-hydroxyvitamin $D_3$ (calcidiol), which in turn is converted into the hormonal form 1,25-hydroxyvitamin $D_3$ (calcitriol) in selected tissues. Calcitriol then binds and activates the cellular Vitamin $D_3$ receptor (VDR) to modulate gene transcription and regulate mineral ion homeostasis. Abrogation of gene activation by VDR action is thought to be under the control of the calcitriol metabolizing enzyme 24-hydroxylase that inactivates calcitriol.

As the VDR receptor (and various isoforms) and the corresponding metabolic enzymes are expressed in many tissues, it is assumed that calcitriol can act in an autocrine, paracrine, or intracrine fashion to affect the biology of non-classical target tissues. For example, production of both the activating and the metabolizing enzymes by cells of the immune system suggests that calcitriol can be locally produced in immune reaction sites. Indeed, recent studies have shown moderate immunosuppressive effect of calcitriol. Other studies have shown that calcitriol may act as a potent antiproliferative agent. For example, Vitamin D deficiency is suspected to raise the risk of prostate cancer, most likely via the VDR but possibly also through its 1-alpha-hydroxylation in the prostate. Similarly, calcitriol is a coordinate regulator of proliferation, differentiation, and survival of breast cancer cells. In addition, epidemiologic, clinical, and animal studies suggested that vitamin D status is important for protection against the development of breast cancer. Therefore, vitamin D compounds that bind and activate VDRs offer promise as therapeutic agents for the treatment of established breast cancer.

To increase levels of calcitriol, various attempts have been undertaken. Most commonly, dietary supplementation using Vitamin $D_3$ (cholecalciferol) is considered a viable option to raise cholecalciferol levels with the expectation that an upstream surplus of substrate will ultimately lead to the production of the calcitriol form. Unfortunately, calcitriol synthesis and degradation are tightly regulated processes, and no significant increase in calcitriol can be achieved using administration of cholecalciferol. Similarly, U.S. Pat. App. No. 2005/0032743 teaches use of low-dose administration of selected boron-containing compounds together with cholecalciferol to raise levels of calcidiol (25-hydroxyvitamin $D_3$) in human, presumably via inhibition of the conversion of the calcidiol to calcitriol. It should be noted that in this publication, calcidiol (but not calcitriol) was described as the 'active form' of vitamin $D_3$. In still other attempts, calcitriol is directly administered (ROCALTROL™; 1,25-dihydroxycholecalciferol, commercially available by Roche) to increase calcitriol serum concentration. However, oral administration of calcitriol is associated with a plethora of undesirable side effects, including hypercalcemia, excessive thirst and sweating, nausea, and constipation.

Thus, while numerous compositions and methods of modulating calcitriol concentrations in serum are known in the art, all of almost all of them suffer from one or more disadvantages. Consequently, there is still a need to provide improved compositions and methods to modulate the concentration of calcitriol in a mammal, and especially in a human.

SUMMARY OF THE INVENTION

The present invention is directed to various compositions and methods of temporarily and transiently increasing blood calcitriol concentration using effective dosages of boron-containing compounds. Most preferably, such compounds are certain carbohydrate-boron complexes with sufficient stability to allow transit into the blood stream upon oral administration.

In one aspect of the inventive subject matter, a method of method of acutely and transiently increasing blood calcitriol concentration in a mammal includes a step of identifying a dosage and schedule for administration of a boron-containing compound that is effective to produce a temporary spike in blood calcitriol concentration in the mammal, and another step of providing the boron-containing compound in a formulation that allows administration of the boron-containing compound in the dosage and schedule effective to produce the temporary spike in the calcitriol concentration in the mammal.

It is generally preferred that the administration is oral administration, most preferably at a daily dosage between 100 mg and 1000 mg of the boron-containing compound. It is further generally preferred that the boron-containing compound is a carbohydrate-boron complex having a boron portion and at least one carbohydrate ligand (e.g., fructose, mannose, mannitol, sorbose, and/or sorbitol) complexed to the boron portion, typically having a boron-ligand association constant of between 3,000 and 20,000. In especially preferred aspects, the boron-ligand association constant that is sufficient to deliver the carbohydrate-boron complex into blood in measurable quantities. Where the complex is electrically charged, it is typically preferred that the charge is neutralized by a alkaline or earth alkaline cation. For example, suitable boron containing complexes include a calcium salt of fructoborate. In further contemplated aspects, it is preferred that the boron-containing compound is formulated such that the temporary spike is measurable between 30 and 180, and more preferably between 60 and 140 minutes post administration.

While not limiting to the inventive subject matter, it is contemplated that the temporary spike (e.g., an increase of at least 5% of blood calcitriol concentration, and more typically at least of at least 25% of blood calcitriol concentration) in the blood calcitriol concentration is produced by activation of blood cells, and especially by activation of monocytes. Therefore, and among other suitable uses, it should be appreciated that contemplated compounds may be effective to modulate an immune response, and especially to reduce an inflammatory reaction.

Therefore, and viewed from a different perspective, a method of modulating a condition associated with a serum calcitriol concentration in a mammal (e.g., an inflammatory reaction or a neoplastic condition) is contemplated that includes the steps of identifying a dosage and schedule for administration of a boron-containing compound that is effective to produce a temporary spike in blood calcitriol concentration in the mammal; and another step of administering the boron-containing compound at the dosage and schedule effective to produce the temporary spike in the calcitriol concentration in the mammal, wherein the temporary spike is effective to modulate the condition.

As before, it is generally preferred that the administration is oral administration, and that the dosage is a daily dosage between 100 mg and 1000 mg of the boron-containing compound. Most preferably, the boron-containing compound is a carbohydrate-boron complex having a boron portion and at least one carbohydrate ligand complexed to the boron portion, typically having a boron-ligand association constant of between 3,000 and 20,000. Consequently, it is also preferred the carbohydrate-boron complex has a boron-ligand association constant that is sufficient to deliver the carbohydrate-boron complex into blood in measurable quantities.

Various objects, features, aspects and advantages of the present invention will become more apparent from the following detailed description of preferred embodiments of the invention.

DETAILED DESCRIPTION

The inventor has unexpectedly discovered that various boron-containing compounds are effective in transiently and acutely raising calcitriol levels in blood of a mammal to a significant degree. Indeed, calcitriol levels could be acutely increased in an amount of at about 80% upon oral administration of a single dose of a boron-containing complex.

In especially preferred aspects of the inventive subject matter, numerous compositions and methods of modulation of calcitriol are provided. Most preferably, the modulation is an acute increase in serum concentration and within a relatively short period of time (e.g., less than 3 hours, and more typically within 90-120 minutes), and is of transient nature (typically lasting less than 12 hours, more typically less than 6 hours, and most typically between 30 and 240 minutes). Most typically, the acute increase is observable as a temporary spike of the calcitriol concentration in the blood/serum, wherein the spike is typically an increase of at least 10% over initial/baseline concentration (more typically at least 20%, even more typically at least 50%, and most typically at least 90%) and limited in duration (e.g., less than 12 hours, more typically less than 8 hours, and most typically less than 4 hours).

Thus, it should be appreciated that contemplated compounds typically produce a transient increase in calcitriol blood/serum concentration rather than a prolonged steady-state increase. Moreover, it should be appreciated that the increase is highly specific towards calcitriol and does not significantly affect 25-hydroxyvitamin $D_3$ (calcidiol). Among other suitable compounds, it is especially preferred that contemplated compounds are boron-ligand complexes, and particularly boron-carbohydrate and/or boron-amino acid complexes. It should be noted that the term "boron-containing compound" as used herein expressly excludes boric acid and any salt thereof.

Therefore, preferred compositions for modulation of calcitriol include a boron-containing compound in which boron or borate is bound (covalently or non-covalently) in a complexed form with at least one ligand, and more typically between two and four ligands. For example, suitable ligands will include those in which at least one of the ligands includes oxygen, nitrogen, carbon, and/or sulfur, and even more preferably in which all of the ligands include at least one of the above atoms. Viewed from a different perspective, ligands are especially preferred where the ligand(s) provide a relatively high association constant, most preferably in the range of about 3,000 to about 20,000.

Among other advantages, it is contemplated that boron complexes with a relatively high association constant will have sufficient stability in vivo to survive the passage through the gastrointestinal system and absorption in to the blood stream in an unaltered form. While not limiting to the inventive subject matter, the inventor hypothesizes that stable boron-containing complexes will interact with certain mammalian cells (and especially monocytes and proximal tubule cells of the nephron) to stimulate 1-alpha hydroxylase, directly or indirectly (possibly via parathyroid hormone receptor PTH1R and/or PTH2R).

Consequently, suitable ligands in contemplated complexes include saccharides (mono-, di-, and poly-) natural and synthetic amino acids, polyols, etc. Thus, especially preferred ligands have a conformation with at least two hydroxyl groups, or one hydroxyl group and one amino group in a 1,2- and a 1,3-position relative to each other. For example, suitable ligands include fructose, sorbitol, mannitol, xylitol, sorbose, serine, threonine, etc. Additionally contemplated boron-containing compounds are described in U.S. Pat. Nos. 5,962,049, 5,985,842, and 6,080,425, and U.S. Pat. App. No. 2005/0032743, all of which are incorporated by reference herein. This and all other extrinsic materials discussed herein are incorporated by reference in their entirety. Where a definition or use of a term in an incorporated reference is inconsistent or contrary to the definition of that term provided herein, the definition of that term provided herein applies and the definition of that term in the reference does not apply.

While synthetic compounds are preferred in at least some aspects of the inventive subject matter, it should be recognized that all naturally-occurring boron/borate-containing compounds are also deemed suitable for use herein. Especially suitable compounds may be isolated from plant materials (and particularly from cell wall associated materials such as polysaccharides), and cartilage and/or bone-associated materials (e.g., glucans, dextrans, etc.) as well as microbial mucopolysaccharides. Of course, it is noted that where desirable, such compounds may also be synthesized mimetics of the above naturally occurring boron and/or borate containing compounds.

Compositions comprising the boron-containing compound may be prepared in numerous manners and may include pharmaceutically and/or nutritionally acceptable carriers. Therefore, it should be recognized that the compounds and compositions according to the inventive subject matter can be modified in numerous manners, and especially preferred modifications include those that improve one or more pharmacokinetic and/or pharmacodynamic parameter. For example, one or more substituents may be added or replaced at the ligands to achieve a higher AUC in serum. On the other hand, and especially where decreased solubility is desired, hydrophobic groups may be added. Moreover, contemplated boron-containing compounds may be modified to so form a prodrug, and exemplary suitable protocols for conversion of contemplated compounds into the corresponding prodrug form can be found in "Prodrugs (Drugs and the Pharmaceutical Sciences: a Series of Textbooks and Monographs)" by Kenneth B. Sloan (ISBN: 0824786297), and "Hydrolysis in Drug and Prodrug Metabolism: Chemistry, Biochemistry, and Enzymology" by Bernard Testa, Joachim M. Mayer (ISBN: 390639025X), both of which are incorporated by reference herein. On the other hand, and especially where contemplated compounds have a higher activity when the compound is metabolized (e.g., partially hydrolyzed, hydroxylated, glucuronidated, etc.), it should be noted that metabolites of contemplated compounds are also expressly contemplated herein.

Depending on the particular purpose, it should also be recognized that contemplated compounds or combinations of compounds may be combined (in vivo or in a pharmaceutical formulation or administration regimen) with further pharmaceutically active ingredients, and especially contemplated other ingredients include known anti-neoplastic, anti-obesity, anti-osteoporosis, anti-stroke, cardioprotective, and/or immunosuppressant medications.

Depending on the particular use and structure, it is therefore contemplated that the compounds according to the inventive subject matter are present in the composition in an amount generally between 1 milligram to 2500 milligrams, more typically between 10 milligrams to 1000 milligrams, and most typically between 250 milligrams to 750 milligrams per single dosage unit. Thus, preferred concentrations of contemplated compounds in vivo or in vitro generally are between 0.1 nM and 500 microM, more typically between 50 nM and 250 microM, and most typically between 100 nM and 250 microM. In particularly preferred aspects, and based on various dose range finding studies, especially preferred oral dosages are between 200 mg and 1000 mg per day, typically in a single dosage (alternatively, up to three daily dosages or even more in rare cases, are also deemed suitable). Unless the context dictates the contrary, all ranges set forth herein should be interpreted as being inclusive of their endpoints, and open-ended ranges should be interpreted to include only commercially practical values. Similarly, all lists of values should be considered as inclusive of intermediate values unless the context indicates the contrary.

Furthermore, it should be recognized that all formulations are deemed suitable for use herein and especially include oral and parenteral formulations. For example, for oral administration, contemplated compositions may be in the form of a tablet, capsule, suspension, or liquid. The nutraceutical or pharmaceutical composition is preferably made in the form of a dosage unit containing a particular amount of the active ingredient. Examples of such dosage units are tablets or capsules. The active ingredient may also be administered by injection as a composition wherein, for example, saline, dextrose or water may be used as a suitable carrier. Alternative suitable routes of administration include oral, intramuscular, intravenous, sublingual, rectal, intradermal, transdermal, topical, or subcutaneous administration. The person of ordinary skill in the art will be well appraised of appropriate nutraceutical and pharmaceutical carriers, and all of the known carriers are deemed suitable for use herein. Especially preferred oral formulations are those in which the boron complex is not retained over a prolonged period, but is bioavailable for absorption in less than 90 after administration. Thus, suitable formulations will include those in which contemplated compounds are packaged into soft gelatin capsules (with other inactive ingredients as appropriate), or are pressed into a tablet (typically in admixture with pharmaceutically acceptable inactive ingredients).

The amount of therapeutically active compound that is administered and the dosage regimen for treating a disease or condition associated with abnormal levels of calcitriol using compounds and/or compositions of this invention depends on a variety of factors, including the age, weight, sex and medical condition of the subject, the severity of the disease, the route and frequency of administration, and the particular compound employed, and thus may vary widely. However, especially suitable quantities are provided above, and may therefore allow for a daily dose of about 0.01 (or even less) to 100 mg/kg body weight, preferably between about 0.1 and about 50 mg/kg body weight and most preferably from about 0.5 to 20 mg/kg body weight. Typically, a daily dose can be administered in one to four doses per day. Especially contemplated conditions that though to be modulated with calcitriol include neoplastic diseases of the prostate and skin, inflammation, conditions associated with overreaction of the immune system (autoimmune diseases, allergic reactions, etc.), diabetes mellitus (type II), cardiac diseases, and obesity.

For therapeutic or prophylactic purposes, contemplated compounds are ordinarily combined with one or more adjuvants appropriate to the indicated route of administration. If administered per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose.

Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Of course, it should further be appreciated that all contemplated compounds may be present in form of a prodrug, a metabolite, and/or a salt with a pharmaceutically acceptable acid or base. The term "prodrug" as used herein refers to a modification of contemplated compounds, wherein the modified compound exhibits less pharmacological activity (as compared to the modified compound) and wherein the modified compound is converted within the body (e.g., in a target cell or target organ) back into the unmodified form through enzymatic or non-enzymatic reactions. For example, conversion of contemplated compounds into prodrugs may be useful where the active drug is too toxic for safe systemic administration, or where the contemplated compound is poorly absorbed by the digestive tract or other compartment or cell, or where the body breaks down the contemplated compound before reaching its target.

With respect to suitable uses, it is generally contemplated that the compositions and compounds according to the inventive subject matter can be employed in the prophylaxis and/or treatment of any condition that is characterized by an abnormal serum concentration (or kinetic) of calcitriol. The term "abnormal serum concentration" as used herein refers to a deviation of at least 20% of the average calcitriol concentration, which is typically below 20 pg/ml, and even more typically below 15 pg/ml. Therefore, especially contemplated uses include all conditions and diseases known to be associated with (permanent or transient) low levels of calcitriol. For example, contemplated uses include prophylactic or therapeutic use of contemplated compounds to treat or prevent various cancers, and especially cancers of the prostate, the mammary gland, and the skin. Moreover, contemplated compounds may also be used to reduce inflammation, or to produce a local or systemic immunomodulation (e.g., change in Th1/Th2 cytokine balance or immunosuppression). Alternatively, suitable uses further include treatment and prevention of diabetes and heart disease, treatment or prevention of obesity.

EXAMPLES

Figure 1A:
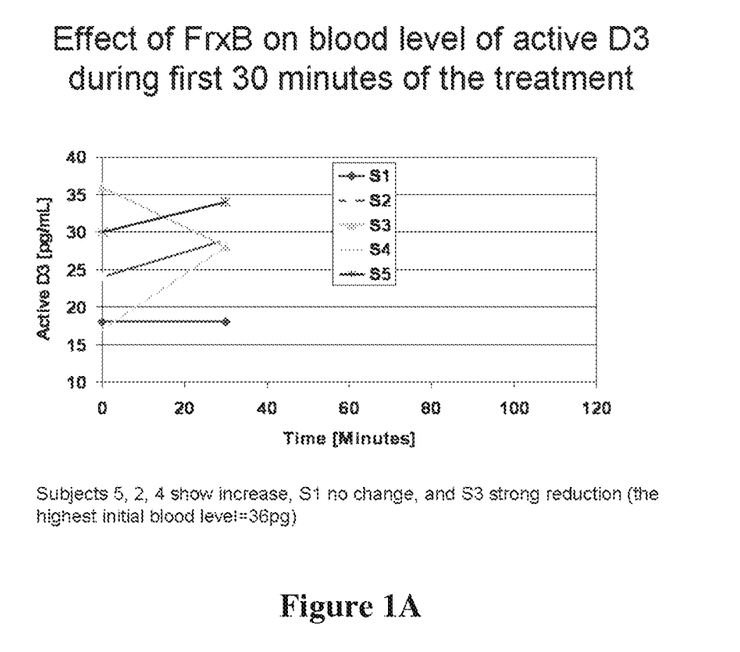
FIGS. 1A-1D are exemplary graphs illustrating changes of calcitriol levels in blood of human volunteers 30 minutes (1A), 60 minutes (1B), 90 minutes (1C), and 90-120 minutes (1D) after administration of contemplated compounds.
Figure 1B:
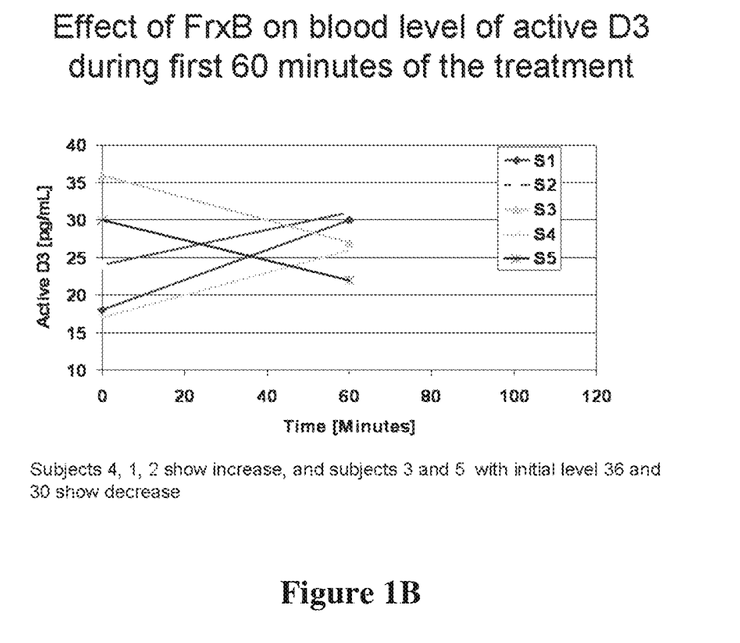
Figure 1C:
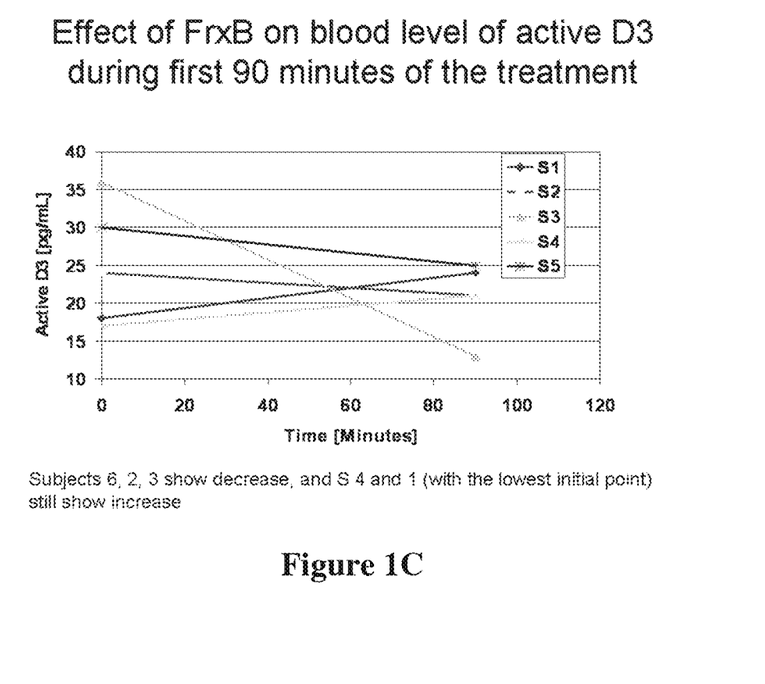
Figure 1D:
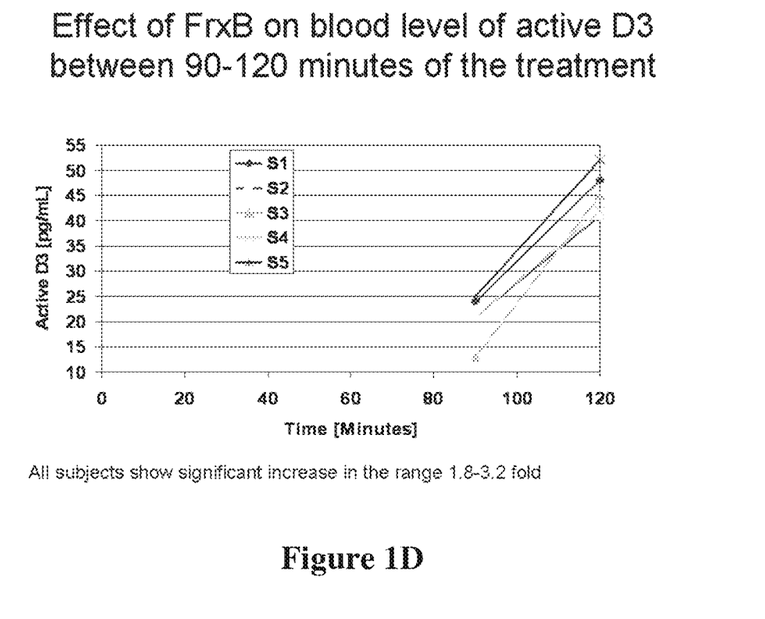

In a typical example, five subjects were administered a single dosage of 552 mg calcium fructoborate upon informed consent, and blood was drawn immediately prior to administration and after 30, 60, 90, and 120 minutes. Calcitriol was measured using a standard radioimmuno assay from a commercial lab starting from 4 ml whole blood (numerous alternative methods are also deemed suitable, including those described in U.S. Pat. Nos. 4,585,741, 5,202,266, and 6,455,714). From each sample and for each time point, concentrations of calcidiol and calcitriol in serum were measured and the data are shown in FIGS. 1A to 1D. FIG. 1A depicts the effect of oral administration of calcium fructoborate on blood calcitriol 30 minutes after oral administration, FIG. 1B depicts the effect of oral administration of calcium fructoborate on blood calcitriol 60 minutes after oral administration, and FIG. 1C depicts the effect of oral administration of calcium fructoborate on blood calcitriol 90 minutes after oral administration. FIG. 1D depicts the effect of oral administration of calcium fructoborate on blood calcitriol 90-120 minutes after oral administration. Remarkably, while calcitriol serum concentration was significantly and acutely affected as can be readily taken from FIGS. 1A-1D, the calcidiol concentration remained unaffected.

Figure 2A:
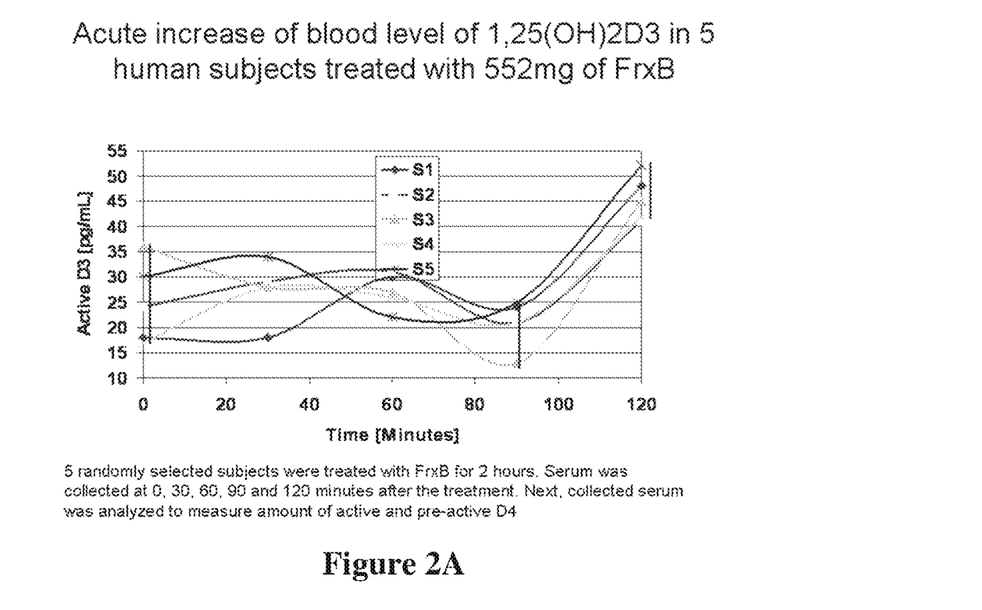
FIGS. 2A-2B are exemplary graphs depicting acute increase of blood calcitriol over time as a function of administration of contemplated compounds.
Figure 2B:
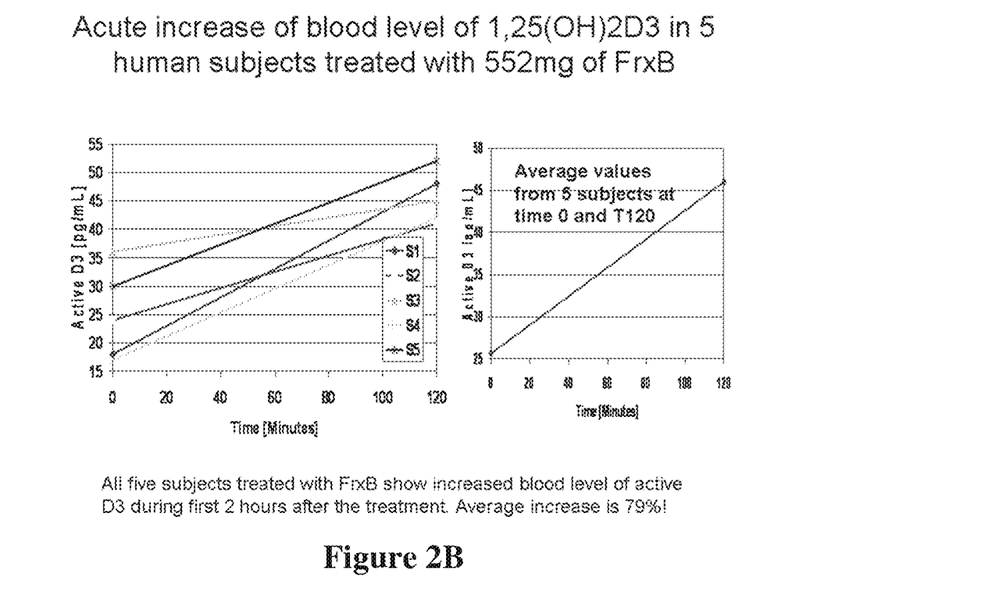
Figure 3:
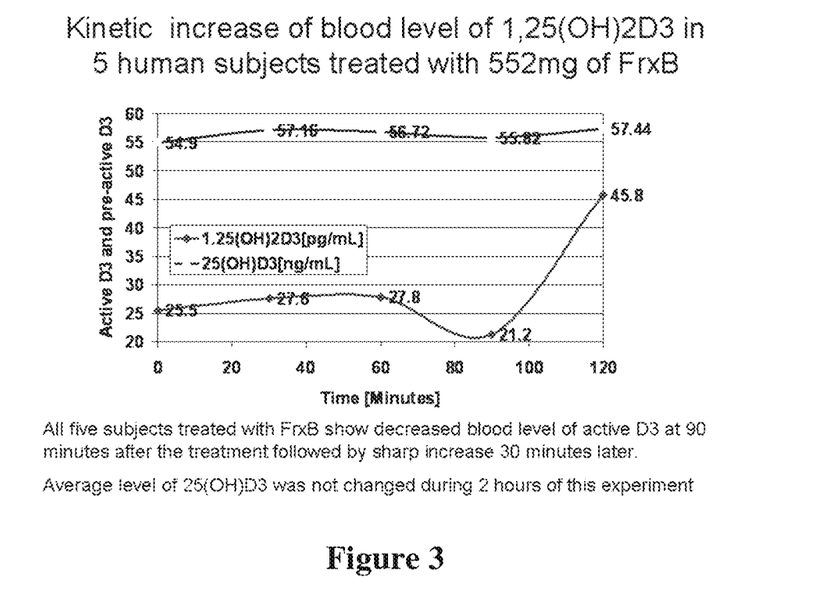
FIG. 3 is an exemplary graph depicting kinetics of blood calcitriol as a function of administration of contemplated compounds.

FIGS. 2A and 2B depict a graphic illustration of the results from this study where the biphasic mode of modulation of calcitriol is clearly seen between times 0-90 minutes (decrease) and 90-120 minutes (increase). In most cases, it is expected that the so increased calcitriol level will drop back to starting levels within 6 hours or less, and more typically within 4 hours, or less (data not shown). FIG. 3 depicts another graphic representation in which the exclusive modulation of calcitriol versus calcidiol is shown.

As the concentration of calcitriol is tightly regulated, it should be appreciated that the stimulatory effect of contemplated compounds is not expected to raise the steady-state level of calcitriol, but rather to provide a pulse of calcitriol (synthesis and/or release). Consequently, contemplated compounds are thought to be particularly useful to provide a transient increase in serum calcitriol without significantly altering serum levels of calcidiol.

While not wishing to be bound by any theory or hypothesis, the inventors contemplate that the compounds according to the inventive subject matter increase serum concentration of calcitriol in a bi-modal manner. During the first 60 minutes, a moderate increase is observed in the case of subjects with low initial level of calcitriol (<30 pg/ml), but not in subjects with initial level >30 pg/ml. Quite likely, activity of the CYP system may play a role during this phase. During the 90-120 minute interval, all subjects responded the same way with a substantial increase regardless of initial calcitriol concentration, which may indicate that the increase in calcitriol may be due to de novo synthesis in the kidney (and possibly ectopically by other tissues and organs). Based on these observations, it should be appreciated that the increase of calcitriol is not a matter of increased stability of calcidiol as postulated earlier. Instead, the increase may be due to a stimulatory effect of contemplated compounds on the kidney and other enzymatically active tissues. Alternatively, or additionally, stimulation by contemplated compounds may also be linked to levels in calcium, phosphate, calcitonin, and/or parathyroid hormone.

Notably, it was observed that the serum calcium and serum phosphate concentrations only changed relatively moderately (about 5-15%) upon administration of contemplated compounds (and especially administration of about 550 mg calcium fructoborate), while the serum concentrations of parathyroid hormone and calcitonin changed at range 10-30% (data not shown).

Among other conditions and disorders that are associated with or responsive to calcitriol, especially contemplated conditions and disorders that may be treated with the boron-containing complexes presented herein are those that require reduction of an immune response (e.g., due to activation of monocytes) to so treat certain inflammatory and/or immune disorders, colorectal cancer, and obesity.

It is still further contemplated that the desirable effect of selectively modulating calcitriol and not affecting calcidiol may be due to the relatively high dosage of contemplated compounds. Therefore, it is contemplated that particularly preferred compositions and methods will include administration of boron-containing compounds at a daily dose of at least 50 mg, more preferably at least 100 mg, even more preferably at least 250 mg, and most preferably at least 500 mg to a achieve a selective modulation of calcitriol. In further, less contemplated aspects of the inventive subject matter, it is noted that in at least some dosage ranges boric acid and any salt thereof may also be employed to modulate the serum calcitriol concentration in a mammal. Thus, it should be appreciated that boron-containing compounds (and to some extent even boric acid and any salt thereof) may be effective in modulation of calcitriol and diseases/conditions associated with abnormal calcitriol levels.

Suitable dosage ranges may be identified by various manners, generally following the experimental protocol as outlined above. Most typically, dosage ranges for a specific route of administration will begin at a low dose (e.g., 0.1 mg/kg) and increase gradually (typically in two- to ten-fold increased of the initial dosage), and effects on blood calcitriol will be observed over several hours following administration. Alternatively, suitable dosage ranges can also be determined by reference to specific literature, and even by reference to this document. Similarly, suitable schedules can be determined without undue experimentation, following the experimental procedures as noted above. Therefore, suitable schedules will typically be between once and four times daily or as otherwise desired.

Using LC-MS, Ca-Fructoborate was detected and measured from serum samples at concentrations as low as 0.2 ppm and higher. This method was used to analyze the presence and amount of Ca-Fructoborate in serum collected from mice treated orally (gavage) with Ca-Fructoborate in liquid at dose 600 mcg/mouse for 30 and 60 minutes. Results show clearly that Ca-Fructoborate was delivered from intestine to bloodstream in intact form and in time-dependent manner, which is reflected in the Table below. The here obtained data show for the first time that Ca-fructoborate can serve as a controlled-release source of boron in blood and tissues and is not likely to be a pre-from of boric acid. Based upon the amount of Ca-fructoborate provided per mouse (20 g by average) the collected results show that bioavailability of the compound is as high as 556 mcg/ml of serum.

| Sample | Time of Treatment | Intact Ca-fructoborate [mcg/mL] |
|---|---|---|
| Untreated | 0 | *below detection |
| 1. | 30 minutes | 449 |
| 2. | 60 minutes | 556 |

*Detection limit - 3 mcg/mL

Detection of intact Ca-Fructoborate in sera collected from fasted mice treated orally with the compound for 30 or 60 minutes. Collected sera were diluted in running buffer and filtered through 0.45 PVDF filter. This solution was analyzed by LCMS for Ca-Fructoborate as the fructoborate anion.

Remarkably, the inventors further contemplate that contemplated compounds additionally had a long-term effect on blood/serum testosterone, particularly where the compounds (typically calcium fructoborate) were administered over extended periods of time. For example, upon administration of 100-600 mg of the boron containing compounds, testosterone levels increased in male and female volunteers at least 15% over base line, more typically at least 20%, and in some cases even more than 25% during administration over at least 14 days.

Consequently, the inventors also contemplate methods of marketing, informing, and advertising a consumer (or patient) that calcitriol levels can be transiently elevated by administration of a boron-containing compound as disclosed and exemplified above. In especially preferred methods, the boron-containing compound is a compound in which boron forms a complex with one or more carbohydrate, polyol, and/or amino acid ligands. Furthermore, it is generally preferred that administration of such compounds is in the range of between 1-2500 mg per day, and more preferably between 100 and 1000 mg per day. With respect to marketing, informing, and advertising, it is noted that all suitable methods are deemed appropriate and include printed matter (e.g., on product package or flyer), displayed matter (e.g., on screen via Internet or TV), and auditory channels (e.g., radio ad).

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A method of treating a condition associated with an abnormal calcitriol level in serum of a mammal, comprising:
    administering a carbohydrate-boron complex to the mammal at a dosage and schedule that transiently increases endogenous blood calcitriol and that simultaneously maintains endogenous blood calcidiol concentration in the mammal; wherein the carbohydrate-boron complex is a fructoborate complex
    wherein the condition is an inflammatory condition or overreaction of the immune system; and
    wherein the dosage and schedule are effective to transiently increase the endogenous blood calcitriol in an amount of at least 20% over baseline.

2. The method of claim 1 wherein the abnormal calcitriol level is an abnormally low level.

3. The method of claim 1 wherein the inflammatory condition is an inflammatory reaction.

4. The method of claim 1 wherein the overreaction of the immune system is an autoimmune disease or an allergic reaction.

5. The method of claim 1 wherein the fructoborate complex is a calcium fructoborate.

6. The method of claim 1 wherein the dosage is at least 250 mg per day.

7. The method of claim 1 wherein the dosage is at least 500 mg per day.

8. The method of claim 1 wherein the dosage is between 200 mg and 1,000 mg per day.

9. The method of claim 1 wherein the dosage and schedule are effective to transiently increase the endogenous blood calcitriol in an amount of at least 50% over baseline.

10. The method of claim 1 wherein the dosage and schedule are effective to concurrently increase endogenous testosterone in an amount of at least 15% over baseline.

11. The method of claim 10 wherein the dosage is between 100 and 600 mg and the schedule comprises administration over at least 14 days.

12. In a method of providing a carbohydrate-boron complex to a mammal, the improvement comprising:
    administering the carbohydrate-boron complex to the mammal after the mammal is found to have an inflammatory condition or overreaction of the immune system;
    wherein the step of administering comprises administration of the carbohydrate-boron complex at a dosage and schedule that transiently increases endogenous blood calcitriol and that simultaneously maintains endogenous blood calcidiol concentration in the mammal; wherein the carbohydrate-boron complex is a fructoborate complex and
    wherein the dosage and schedule are effective to transiently increase the endogenous blood calcitriol in an amount of at least 20% over baseline.

13. The method of claim 12 wherein the dosage and schedule are effective to also concurrently increase endogenous testosterone in an amount of at least 15% over baseline.

14. The method of claim 13 wherein the dosage is between 100 and 600 mg and the schedule comprises administration over at least 14 days.

15. The method of claim 12 wherein the dosage is at least 500 mg per day.

16. The method of claim 12 wherein the inflammatory condition is an inflammatory reaction, or wherein the overreaction of the immune system is an autoimmune disease or an allergic reaction.

17. The method of claim 12 wherein the endogenous blood calcitriol is abnormally low.

18. The method of claim 12 wherein the carbohydrate-boron complex is a calcium fructoborate.

\* \* \* \* \*